US006013433A

United States Patent [19]
Pellett et al.

[11] Patent Number: 6,013,433
[45] Date of Patent: Jan. 11, 2000

[54] BACULOVIRUS EXPRESSION VECTORS AND RECOMBINANT ANTIGENS FOR DETECTING TYPE-SPECIFIC ANTIBODIES TO HERPES SIMPLEX VIRUS

[75] Inventors: Philip E. Pellett, Stone Mountain; Demetrio Sanchez-Martinez, Atlanta, both of Ga.

[73] Assignee: The United States of America as represented by the Secretary of the Department of Health and Human Services, Washington, D.C.

[21] Appl. No.: 08/472,507

[22] Filed: Jun. 7, 1995

Related U.S. Application Data

[62] Division of application No. 07/691,728, Apr. 26, 1991.
[51] Int. Cl.$^7$ ............................ C12Q 1/70; G01N 33/53; C12P 21/06; C12P 19/34
[52] U.S. Cl. .............................. 435/5; 435/7.1; 435/69.1; 435/71.1; 435/91.33; 530/350; 530/389.1; 530/388.3; 530/395
[58] Field of Search ................................ 435/5, 7.1, 69.1, 435/71.1, 91.33; 530/350, 389.1, 388.3, 395

[56] References Cited

PUBLICATIONS

Ashley et al. J. Clin. Microbiol. 26(4): 662–667, 1988.
Lee et al. (AA1) J. Clin. Microbiol. 22(4): 641–644, 1985.
Lee et al. (AW) J. Virol. Methods 14: 111–118, 1986.
Krishna et al. J. Gen. Virol. 70: 1805–1814, 1989.
Matsuura et al. J. Gen. Virol. 68: 1233–1250, 1987.
Luckow et al. Bio/Technology 6: 47–55, 1988.
Sanchez–Martinez et al. Virology 182:229–238, 1991.
Demetrio Sanchez–Martinez et al., "Expression of HSV–1 and HSV–2 glycoprotein G in Insect Cells by Using a Novel Baculovirus Expression Vector," *Virology*, 182:229–238 (1991).
Demetrio Sanchez–Martinez et al., "Evaluation of a Test Based on Baculovirus–Expressed glycoprotein G for Detecction of Herpes Simplex Virus Type–Specific Antibodies," *The Journal of Infectious Disease*, 164:1196–1199 (1991).
Deborah L. Parkes et al., "Seroreactive Recombinant Herpes Simplex Virus Type 2–Specific Glycoprotein G," *Journal of Clinical Microbiology*, vol. 29(4):778–781 (Apr. 1991).
Demetrio Sanchez–Martinez et al., "Expressionof HSV–1 and HSV–2–Glycoprotein G in Insect Cells by Using the Baculovirus Expression System," *Abstract for International Herpes Virus Workshop*, Georgetown University, Washington, D.C. (Aug. 2, 1990).
Verne A. Luckow et al., "High Level Expressionof Nonfused Foreign Genes with *Autographa californica* Nuclear Polyhedrosis Virus Expression Vectors," *Virology*, 170:31–39 (1989).

Demetrio Sanchez–Martinez et al., "Expression of HSV–1–and HSV–2–Glycoprotein G In Insect Cells by Using A Baculovirus Transfer Vector," *Presented at the American Society for Virology Annual Meeting*, London, Ontario (Jul. 10, 1989).
Lois K. Miller, "Baculoviruses as Gene Expression Vectors," *Ann. Rev. Microbiol.*, 42:177–199 (1988).
D.J. McGeoch et al., "The Complete DNA Sequence of the Long Unique Region In the Genome of Herpes Simplex Virus Type I," J. Gen. Virol., 69:1531–1574 (1988).
Rhoda L. Ashley et al., "Comparison of Western Blot (immunoblot) and Glycoprotein G–Specific Immunodot Enzyme Assay for Detecting Antibodies to Herpes Simplex Virus Types 1 and 2 in Human Sera," *Journal of Clinical Microbiology*, 26(4):662–667 (Apr. 1988).
Verne A. Luckow et al., "Trends in the Development of Baculovirus Expression Vectors," *Bio/Technology*, 6:47–55 (Jan. 1988).
Yoshiharu Matsuura et al., "Baculovirus Expression Vectors: the Requirements for High Level Expression of Proteins, Including Glycoproteins," *J. gen. Virol.*, 68:1233–1250 (1987).
Dunan J. McGeoch et al., "DNA Sequence and Genetic Content of the Hindlll/Region in the Short Unique Component of the Herpes Simplex Virus Type 2 Genome: Identification of the Gene Encoding Glycoprotein G, and Evolutionary Comparisons," J. gen. Virol., 68:19–38 (1987).
Veronica Sullivan et al., "Expression and Characterization of Herpes Simplex Virus type 1 (HSV–1) glycoprotein G (gG) by Recombinant Vaccinia Virus: Neutralization of HSV–1 Infectivity with Anti–gG Antibody," *J. gen. Virol.*, 68:2587–2598 (1987).
Max D. Summers et al., "A Manual of Methods for Baculovirus Vectors and Insect Cell Culture Procedures," *Texas Agricultural Experiment Station and Texas A& M University, College Station, Texas* (May 1987).
Henry K. Su et al., "Processing of the Herpes Simplex Virus Type 2 glycoprotein gG–2 Results in Secretion of a 34,000–M, Cleavage Product," *Journal of Virology*, 61(g5):1735–1737 (May 1987).
M.C. Frame et al., "Novel Herpex Simplex Virus type 1 Glycoproteins Identified by Antiserum against a Synthetic Oligopeptide from the Predicted Product of Gene US4," *J. gen. Virol.*, 67:745–751 (1986).
Mathias Ackermann et al., "Identification, Properties, and Gene Locationof Novel Glycoprotein Specified by Herpres Simplex Virus 1," *Virology*, 150:207–220 (1986).

(List continued on next page.)

*Primary Examiner*—Donna C. Wortman
*Assistant Examiner*—May K. Zeman
*Attorney, Agent, or Firm*—Jones & Askew, LLP

[57] ABSTRACT

Novel baculovirus expression vectors and recombinant antigens for detecting, type-specific herpes simplex virus (HSV) infection have been made. Diagnostic kits and assays for detecting type-specific HSV infection have been described. High level production of foreign proteins in substantially pure form are now made possible by the novel baculoviruses of the present invention.

2 Claims, 7 Drawing Sheets

OTHER PUBLICATIONS

Francis K. Lee et al., "A Novel Glycoprotein for Detection of Herpes Simplex Virus type 1–specific Antibodies," *Journal of Virological Methods*, 14:111–118 (1986).

Andre J. Nahmias et al., "Monoclonal Antibody ImmunoafinityPurlified glycoproteins for the Detection of Herpes Simplex Virus Type 1 and Type 2 Specific Antibodies In Serum," *Immunology*, pp. 203–210 (1986).

Douglas D. Richman et al., "Identification of a New Glycoprotein of Herpes Simplex Virus Type 1 and Genetic Mapping of the Gene that Codes for It," *Journal of Virology*, 5(2):647–655 (Feb. 1986).

Gale E. Smith et al., "Modification and Secretion of Human Interleukin 2 produced in Insect Cells by a Baculovirus Expression Vector," *Proc. Natl. Acad. Sci. USA*, 82:8404–8408 (Dec. 1985).

Francis K. Lee et al., "Detection of Herpes Simplex Virus Type 2–Specific Antibody with Glycoprotein G," *Journal of Clinical Microbology*, 22(4):641–644 (Oct. 1985).

Luis F. Carbonell et al., "Baculovirus–Mediated Expression of Bacterial Genes in Dipteran and Mammalian Cells," *Journal of Virology*, 56:(1)153–160 (Oct. 1985).

N. Balachadran et al., "Synthesis and Processing of Glycoprotein gG of Herpes Simplex Virus Type 2," *Journal of Virology*, 54(3):825–832 (Jun. 1985).

Bernard Roizman et al., "Identification and Preliminary Mapping with Monocional Antibodies of a Herpes Simplex Virus 2 Glycoprotein Lacking a Known Type 1 Counterpart," *Virology*, 133:242–247 (1984).

H.S. Marsden et al., "Characterization of the 92,000–Dalton Glycoprotein Induced by Herpes Simplex Virus Type 2," *Journal of Virology*, 50(2):547–554 (May 1984).

Marilyn Kozak, "Possible Role of Flanking Nucleotides in Recognition of the AUG Initiator Codon by Eukaryotic Ribosomes," *Nucleic Acids Research*, 9(20):5233–5252 (1981).

Lawrence S. Morse et al., "Anatomy of Herpes Simplex Virus DNA," *Journal of Virology*, 24:(1)231–248 (Oct. 1977).

Michael T. Bernstein et al, "Method for Typing Antisera to *Herpesvirus hominis* by Indirect Hemagglutination Inhibition," *Applied Microblology*, 21(4):680–684 (Apr. 1971).

Andre J. Nahmias et al., "Antiboides to Herpesvirus Hominis Types 21 and 2 in Humans," *American Journal of Epidemiology*, 91(6):539–546 (1970).

Pilarica M. Ejercito et al., "Characterization of Herpes Simplex Virus Strains Differing in their Effects on Social Behaviour of Infected Cells," *J. gen. Virol.*, 2:357–364 (1968).

Andre J. Nahmias et al., "Antigenic and Biologic Differences in *Herpesvirus hominis*," *Virology*, 10:110–159 (1968).

BACULOVIRUS EXPRESSION VECTORS AND RECOMBINANT ANTIGENS FOR DETECTING TYPE-SPECIFIC ANTIBODIES TO HERPES SIMPLEX VIRUS

This application is a division of application Ser. No. 07/691,728, filed Apr. 26, 1991 which status is pending.

The present invention is related generally to recombinant DNA technology. More particularly, the present invention is related to the construction of novel baculovirus transfer vectors for efficient expression of foreign genes and to the construction of novel baculoviruses expressing herpes simplex virus (HSV) glycoproteins gG-1 and gG-2.

BACKGROUND OF THE INVENTION

Baculovirus (*Autoarapha californica*) has been used for the expression of foreign proteins (Luckow et al, 1988, Biotech. 6:47–55; Luckow et al, 1989 Virol. 170: 31–39). However, a consistent level of foreign gene expression approaching that of the native polyhedrin has not been achieved by heretofore constructed baculovirus systems.

SUMMARY OF THE INVENTION

It is, therefore, an object of the present invention to provide a novel gene transfer vector that enables the construction of recombinant baculoviruses, the DNA sequence of which mimics the 5' nontranslated leader sequence of the wild-type baculovirus polyhedrin gene, whereby the expression efficiency of the foreign gene approaches that of the wild-type polyhedrin gene.

It is another object of the present invention to obtain isolated, substantially pure, HSV glycoproteins, gG-1 and gG-2, from insect cells infected with the baculovirus expression systems of the present invention.

It is a further object of the present invention to provide baculovirus-expressed antigens for HSV serodiagnostic tests differentiating between HSV-1 and HSV-2 antibodies.

An additional object of the present invention is to provide a diagnostic kit for performing type-specific serologic tests to detect HSV infection.

A still further object of the present invention is to provide a composition, comprising immunoreactive amount of HSV glycoprotein G in a pharmaceutically acceptable carrier.

Other objects and advantages will become evident from the following detailed description of the invention.

BRIEF DESCRIPTION OF THE DRAWINGS

The above and other objects, features and many of the attendant advantages of the invention will be better understood upon a reading of the following detailed description when considered in connection with the accompanying drawing wherein:

FIG. 1 (A) shows synthetic oligomers used in the construction of the baculovirus gene transfer vectors and the gG-1- and gG-2-expressing recombinant baculoviruses. As described herein, oligoduplex AB (SEQ ID NO:1 and SEQ ID NO:2) was used in the construction of pPP-2, oligoduplex V78 (SEQ ID NO:3) in pAcDSM, oligoduplex SR34 (SEQ ID NO:4) AcDSMgG-1, and oligoduplex D34 (SEQ ID NO:5) in AcDSMgG-2. Relevant restriction endonuclease sites are indicated. (B) Schematic representation of the method of inserting a foreign gene into the transfer vector pAcDSM. (C) Comparison of nucleotide sequences in the 5' non translated region of the wild type baculovirus (AcNPV) (SEQ ID NO:8) and the recombinant viruses Ac373' gG-1 (SEQ ID NO:8) and AcDSMgG-1(SEQ ID NO:9). Extraneous nucleotides relative to the wild type polyhedrin sequence are boxed.

FIG. 2 demonstrates DNA hybridization analysis of recombinant baculoviruses. (A) Analysis of Ac373'gG-1. Whole cell DNA extracted from Sf9 cells infected with AcNPV (lanes 1) or Ac373'gG-1 (lanes 2), and DNA of the recombinant transfer plasmid pAc373'gG-1 (lanes 3) were digested with SalI, separated in 0.8% agarose gels, blotted bidirectionally to nitrocellulose membranes, then hybridized with the indicated probes. A photograph of an ethidium bromide stained gel is included for reference. (B) and (C), analysis of AcDSMgG-1 and AcDSMgG-2, respectively. The experiments were as in panel A with the substitution of the recombinant virus in lanes 2 (AcDSMgG-1 and AcDSMgG-2, respectively) and the recombinant transfer plasmid in lanes 3 (pAcDSMgG-1 and pAcDSMgG-2, respectively). Polyhedrin-gene flanking fragments are marked with empty triangles. The fragment containing the polyhedrin gene is marked with full triangles. Fragments carrying gG-1 or gG-2 are indicated with arrows. The size standard is a HindIII digest of phage lambda.

FIG. 3 shows the synthesis and processing of tbaculovirus expressed gG-1. (A) Immunoblots of proteins extracted at 100 h p.i. (hours post infection) from equal numbers of (Ac373'gG-1, AcDSMgG-1 and AcNPV) infected or uninfected Sf9 cells were separated by SDS-PAGE in 11% gels, transferred to nitrocellulose membranes, then reacted with the indicated antibodies. (B) Quantitative comparison of the amount of gG-1 expressed in Sf9 cells by the recombinants Ac373'gG-1 and AcDSMgG-1. Cell extracts treated as in A were 4-fold-serially diluted in 0.01M PBS (pH 7.4), bound to a nitrocellulose membrane using a slot blot apparatus, and reacted with gG-1 specific monoclonal antibody (H1379). (C) Time course of the synthesis of gG-1 in Ac373'gG-1 and AcDSMgG-1 (Lanes a and b, respectively) infected Sf9 cells. Cells were harvested at the indicated times, treated as in A and reacted with a HSV-1-positive human serum specimen. (D) Immunoblot of proteins extracted from Sf9 cells infected with AcDSMgG-1 grown in the presence (+) or the absence (−) of 3 μg/ml tunicamycin from 24 h p.i. until 54 h p.i. Blots were reacted with gG-1 specific monoclonal antibody (H1379). (E) Immunoblot analysis of proteins extracted from Sf9 cells infected with AcDSMgG-1 and from HEp-2 cells infected with HSV-1(F). The positions of the molecular mass standards are shown on the side of each panel, (myosin, 200 kDa; β-galactosidase 116.3 kDa; phosphorylase B, 97.4 kDa; bovine serum albumin, 66.2 kDA; ovalbumin, 42.7 kDa; and carbonic anhydrase, 31 kDa). In all the panels the apparent molecular mass of bands discussed in the text (arrows) is indicated.

FIG. 4 shows the synthesis and processing of baculovirus expressed gG-2. (A) Immunoblots of proteins extracted at 100 h p.i. separated in a 9% SDS-PAGE gel then transferred to nitrocellulose and reacted with the indicated antibodies. (B) Time course of the synthesis of gG-2 in AcDSMgG-2 infected Sf9 cells. Proteins extracted from cells harvested at the times indicated were treated as in A, then reacted with gG-2-specific-monoclonal antibody (H1206). (C) Immunoblot of proteins extracted from Sf9 cells infected with AcDSMgG-2 grown in the presence (+) or the absence (−) of 3 μg/ml tunicamycin from 24 h p.i. until 54 h p.i. Blots were reacted with gG-2 specific monoclonal antibody (H1206). (D) Immunoblot analysis of proteins extracted from Sf9 cells infected with AcDSMgG-2 and from HEp-2 cells infected with HSV-2(G). In all the panels, the apparent molecular mass of bands discussed in the text (arrows or triangles) is indicated. Molecular mass standards, on the side of each panel, are as described in FIG. 3.

DETAILED DESCRIPTION OF THE INVENTION

The above and various other objects and advantages of the present invention are achieved by a transfer vector which enables juxtaposition of a foreign gene desired to be expressed, with the baculovirus polyhedrin gene precisely at the translation initiation site without missing any nucleotide present in the 5' region of the wild-type polyhedrin gene or without adding any extraneous nucleotides at said translation initiation site. A recombinant baculovirus constructed with this transfer vector expresses the foreign gene at a higher level than the recombinant baculovirus constructed using a vector that has extraneous nucleotides in the above mentioned 5' region.

Two baculovirus gene transfer vectors were constructed: (1) pPP-2 and (2) pAcDSM. pPP-2 can be used to construct gene fusions at any of the three reading frames. It is noted that after construction of the expression cassette in pPP-2, the reconstructed gene must be transferred to another baculovirus gene transfer vector to acquire the flanking sequences necessary for insertion into the baculovirus genome.

pAcDSM, on the other hand, allows the construction of recombinant baculoviruses with the 5' nontranslated leader sequence of the polyhedrin gene joined at the coding region of the foreign gene precisely at the translation initiation codon, with no missing or extraneous nucleotides. No similar vector has heretofore been made or described.

It is noted that the designations AcDSMgG-1 and AcDSMgG-2 refer to recombinant baculoviruses which express gG-1 and gG-2 glycoproteins of HSV types 1 and 2, respectively.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

The term "substantially pure" protein as used herein means that the protein is obtained in as pure a form as is necessary for the purpose for which it is to be employed by using conventional isolation and purification techniques well known to one of ordinary skill in the art and is free from undesirable impurities or contaminants.

The term "foreign gene" as used herein means a heterologous gene that is desired to be expressed by the recombinant baculovirus of the present invention.

Materials and Methods

Cells and viruses. ACNPV (*Autographa californica* nuclear polyhidrosis virus) and recombinant baculoviruses were grown and assayed in a continuous ovarian cell line (Sf9) derived from *Spodoptera frugiperda* (fall armyworm) as described by Summers and Smith, Texas Agricultural Experiment Station Bulletin No. 1555, 1987. Sf9 cells (ATCC No. CRL 1711) were obtained from the American Type Culture Collection (Rockville, Md.). Wild type AcNPV and the gene transfer vector pAc373 (Smith et al Proc. Natl. Acad. Sci. U.S.A. 82:8404–8408, 1985) were obtained from Dr. Max Summers (Texas A&M University; College Station, Tex.). HSV-1(F) and HSV-2(G) (Ejercito et al, 1968) were obtained from Dr. Bernard Roizman (University of Chicago, Chicago, Ill.) and grown and propagated as described (Morse et al, 1977). Monoclonal antibodies specific for gG-1 (H1379) (Lee et al, 1986) and specific for gG-2 (H1206) (Lee et al, 1985) were obtained from Dr. Lenore Pereira (University of California at San Francisco, San Francisco, Calif.).

DNA Manipulations. DNA manipulations were carried out as described by Maniatis et al, 1982. Restriction endonucleases and T4 DNA polymerase were purchased from New England BioLabs (Beverly, Mass.), Mung bean exonuclease from Pharmacia LKB Biotechnology Inc. (Piscataway, N.J.), and T4 DNA ligase from Boehringer-Mannheim Biochemicals (Indianapolis, Ind.). Oligonucleotides were synthesized in a model 380 DNA synthesizer from Applied Biosystems (Foster City, Calif.).

Figure 1A:
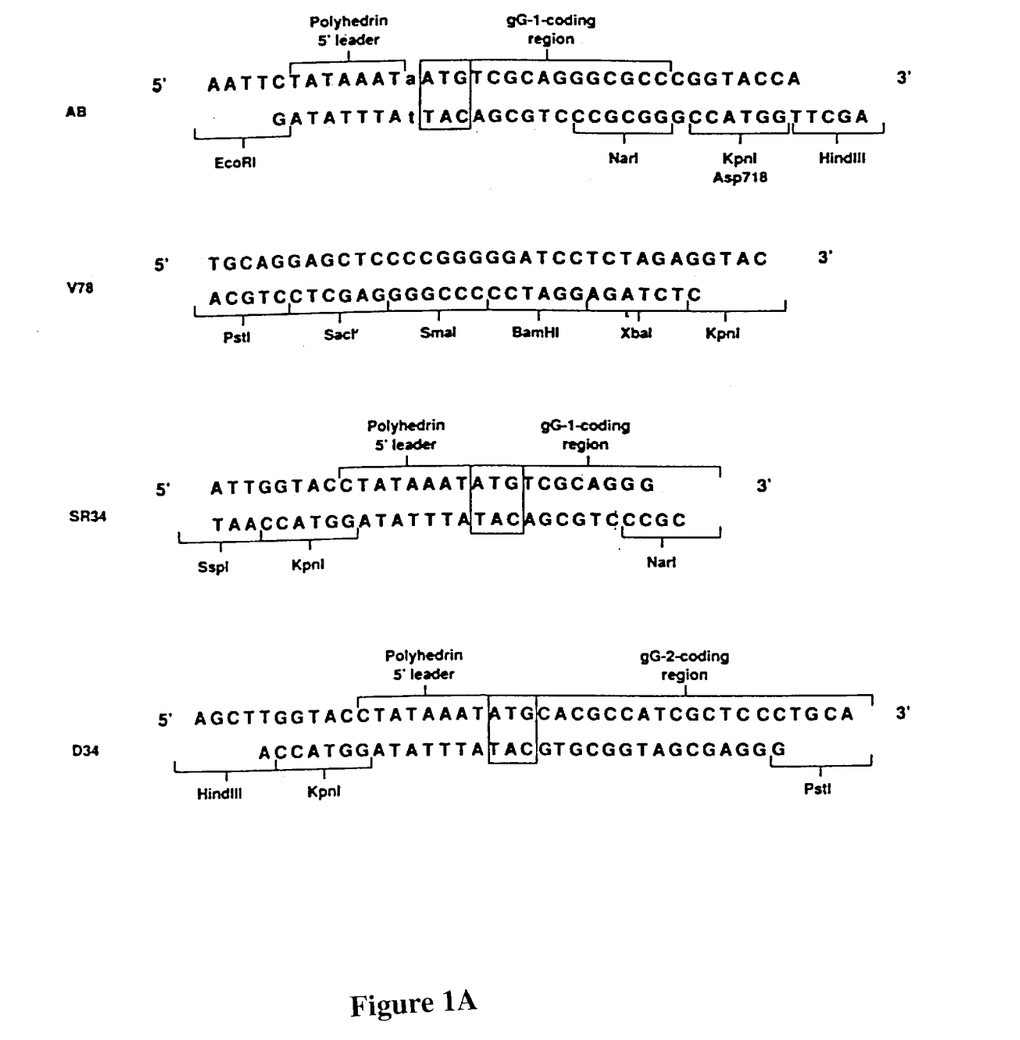

Construction of modified gene transfer vector pPP-2. pPP-2 was constructed by digesting pUC8 with NarI, filling in the overhanging 5' nucleotides using T4 DNA polymerase, then self ligation, resulting in the elimination of the NarI site generating pPP-1. A synthetic oligoduplex AB (SEQ ID NO:1and SEQ ID NO:2) (FIG. 1A) was ligated between the EcoRI and HindIII sites of pPP-1, to obtain pPP-2.

pAcDSM. pAc373 was digested to completion with SalI and KpnI. The DNA fragment spanning the region between 3.18 and 4.43 kbp in the coordinate system of Summers and Smith, 1987, supra, was purified from agarose and inserted into pUC19 which had previously been digested with the same enzymes. The resulting plasmid (pDM1) was linearized by digestion with AvaI. After PEG precipitation (Sadhu and Gedamu, BioTechniques, 6:20–21, 1988), 5' overhanging nucleotides were removed by digestion with 150 units of Mung bean exonuclease/µg of DNA to obtain blunt ends, followed by KpnI digestion. A synthetic oligoduplex, V78 (SEQ ID NO:3) (FIG. 1A), was inserted between the KpnI site and the blunt end (nucleotide −9 of the 5' leader sequence of the polyhedrin gene) of pDM1 to obtain pDM2. The fidelity of the construct was checked by nucleotide sequencing using primers flanking the cloned fragment. pDM2 was digested with EcoRV and KpnI. The resulting 118 bp fragment was ligated to pAc373 previously digested with the same enzymes to obtain the transfer vector pAcDSM.

Cloning gG-1 and gG-2 into baculovirus transfer vectors. For convenience, the nucleotide sequence coordinates reported for the genomic sequence of HSV-1 strain 17 (McGeoch et al, J. Gen. Virol. 69:1531–1574, 1988) and for the HindIII L fragment of HSV-2 strain HG52 (McGeoh et al, J. Gen. Virol. 68:19–38, 1987) are used throughout this application. HSV-1 strain F (HSV-1(F)) and HSV-2 strain G (HSV-2(G)) DNAs were separately digested to completion with BamHI and shotgun cloned into pUC19. Plasmids carrying HSV-1(F) BamHI J (pH1F-110, nucleotides 136285 to 142742) and HSV-2(G) BamHI L (pH2G-112, nucleotides 2356 to 6894) fragments, which contain the intact gG-1 and gG-2 genes, respectively, were used as the starting point for engineering the genes for compatibility with the transfer vectors.

gG-1 insertion into pPP-2. pH1F-110 was digested with SphI to remove nucleotides 137617 to 142742 of the HSV-1 fragment (removing two of the three NarI sites in the insert), and ligated to itself. The resulting plasmid (pH1F-1001) was digested with NarI and religated to itself, deleting nucleotides 136285 to 136749 and a small portion of the vector, resulting in p1HF-1002. This plasmid was digested with NarI and HindIII, and the 873 bp fragment carrying the nearly complete gG-1 gene (nucleotides 136749 to 13762) was ligated to plasmid pPP-2, which had previously been digested with NarI and HindIII. The resulting plasmid (pH1F-1011) was digested with EcoRI and HindIII, made blunt ended with T4 DNA polymerase, and ligated to pAc373 which had been digested with BamHI and made blunt ended by treatment with T4 DNA polymerase. A plasmid containing the gG-1 gene inserted in the proper orientation was designated pAc373'gG-1.

gG-1 insertion into pAcDSM. The 871 bp fragment between the NarI and SphI sites of pH1F-1002 (nucleotides 136749 to 137620), carrying the nearly complete gG-1 gene, was ligated to pUC18 which had previously been digested with the same enzymes. The resulting plasmid, pSR1, was digested with NdeI and BamHI, obtaining a 944 bp fragment that was ligated to pUC 9 which had been previously digested with the same enzymes, resulting in pSR3. A synthetic oligoduplex, SR 34 (SEQ ID NO:4) (FIG. 1A), was ligated between the SspI and NarI sites of pSR3. The resulting construct, plasmid pSR5, was successively incubated with KpnI, T4 DNA polymerase and BamHI, and ligated with the vector pAcDSM which had previously been successively digested with PstI, T4 DNA polymerase and BamHI. The resulting plasmid was designated pAcDSMgG-1.

gG-2 insertion in pAcDSM. pH2G-112 was digested with BamHI and PvuII, to obtain a 3722 bp fragment which was purified from agarose and ligated with pUC19 which had been digested with BamHI and SspI. The resulting plasmid, pDS1, was digested with PstI and HindIII and ligated with a synthetic oligoduplex, D34 (SEQ ID NO:5) (FIG. 1A), to generate pDS2. The 1316 bp fragment resulting from digesting pH2G-112 with HincII was purified from agarose, and successively reacted with BstNI, T4 DNA polymerase and StyI. The resulting 161 bp fragment was purified from agarose then ligated to pDS2, which had previously been successively incubated with PstI, T4 DNA polymerase, and StyI. The resulting plasmid, pDS6, was digested with SspI and XhoI and ligated to an agarose-purified 2148 bp fragment obtained by digesting pH2G-112 with SspI and XhoI. The resulting plasmid, pDS7, was digested with HindIII and XhoI. The resulting 2311 bp fragment (carrying the complete gG-2 gene) was ligated with pUC9 which had been digested with HindIII and SalI. The resulting plasmid, pDS8, after successive reactions with KpnI, T4 DNA polymerase and BamHI, was ligated with pAcDSM which had been successively reacted with PstI, T4 DNA polymerase and BamHI, to obtain pAcDSMgG-2.

Transfection and Selection of Recombinant baculoviruses. Standard procedures were used for transfection, selection of recombinant baculoviruses, and virus titration (See for example Summers and Smith, 1987, supra). Recombinant viruses were plaque purified at least five times.

Extraction of viral DNA and Hybridization Analysis.

Whole infected-cell DNA (Sulmners and Smith, 1987, supra.), was digested to completion with SalI and resolved by electrophoresis in 25 cm long 0.8% agarose gels (Seakem, FMC BioProducts, Rockland, Me.). Replica blots were obtained by blotting bidirectionally onto nitrocellulose paper (BA 85, Schleicher and Schuell, Keene, N.h.) (Southern, J. Mol. Biol. 98:503–517, 1975). Prehybridization was for 4 hours in 200 $\mu$g/ml heparin (Sigma, St. Louis, Mo.), 5× SSC (1× SSC: 0.15 M NaCl, 0.015 M sodium citrate) and 0.1% SDS at 65° C. Hybridization was in fresh buffer using probes labeled with [$^{32}$P] by nick translation. After washing the blots at room temperature (22–24° C.), they were incubated for one hour in 0.2× SSC plus 0.1% SDS at 65° C., then air dried prior to autoradiography.

Protein analysis by immunoblots. Sf9 cells were grown in either Hink's medium supplemented with 10% fetal calf serum according to Summers and Smith 1987, supra, or in serum free medium (EX-CELL 400, J. R. Scientific, Woodland, Calif.) and infected with recombinant or wild-type baculoviruses at multiplicity of infection of 10 PFU/cell in 25 cm$^2$ flasks at 27° C. After 1.5 hours, the inoculum was removed and replaced with fresh medium. At the appropriate times post-infection, the cells were scraped from the flask and harvested by centrifugation for 10 minutes at 1500×g and 4° C. The pellet was resuspended in disruption buffer (5.7 M urea, 2.8% SDS, and 1.8 M 2-mercaptoethanol), sonicated for 30 seconds (output control 4, duty cycle 50%) in a cup horn sonicator (Model W-375, Heat Systems-Ultrasonic, Inc., Farmingdale, N.Y.), and heated for 3 minutes at 95° C. Proteins were separated by electrophoresis in polyacrylamide gels (acrylamide to bis-acrylamide ratio of 37.5:1), and then electrically transferred onto nitrocellulose paper (Schleicher and Schuell BA85) using 0.1% SDS in the transfer buffer. Blots were incubated for 1 hour in blotto (5% skim milk, phosphate-buffered saline 0.01 M [pH 7.4], 0.05% Tween 20), then incubated for 1 hour in fresh blotto containing the appropriate dilution of either human serum or monoclonal antibody. After three 10 min. washes in 0.05% Tween 20 in phosphate-buffered saline, blots were incubated with alkaline-phosphatase-conjugated-goat-anti-human or alkaline-phosphatase-conjugated-goat-anti-mouse IgG (BioRad, Rockville Centre, N.Y.) in 0.05% Tween 20 in phosphate-buffered saline for 2 hours, washed 3 times for 10 minutes with the same buffer, and developed with p-nitro blue tetrazolium chloride and 5-bromo-4-chloro-3-indoyl phosphate p-toluidine salt (BioRad) according to the vendor's protocol.

Results

Vector construction. Two gene transfer vectors were constructed, pPP-2, which incorporates the nucleotides −7 to −1 of the 5' nontranslated leader sequence of the polyhedrin gene missing in the widely used transfer vector pAc373 (Smith et al, 1985, supra), but which results in recombinant baculoviruses containing at least 21 extraneous nucleotides in this region, and pAcDSM, which allows the construction of recombinant baculoviruses with the 5' nontranslated leader sequence of the polyhedrin gene joined precisely to the coding region of the foreign gene at the translation initiation codon, with no missing or extraneous nucleotides.

DPP-2. pPP-2 was useful particularly for the expression of gG-1, but has several features which allow it to be used in a more general manner for the construction of gene cassettes for insertion into baculovirus gene transfer vectors such as pAc373 and pAc6lo which were designed for linking foreign genes to the polyhedrin gene via their 5' nontranslated sequences. pPP-2 restores sequences immediately preceding the polyhedrin translation initiation site which are missing in these vectors, but have been shown to be of great importance in controlling translation efficiency in many eucaryotic systems (Kozak, Nucleic Acids Res. 9:5233–5252, 1981), including baculovirus (Matsuura et al, J. Gen. Virol. 68:1233–1250, 1987). pPP-2 is a plasmid carrying a sequence composed of, in order, nucleotides -7 to -1 of the 5' nontranslated leader sequence of the polyhedrin gene, an extra A residue, an initiation codon, the first twelve nucleotides of the gG-1 gene which includes a NarI site, and an additional KpnI/Asp718 site which is not present in the gG-1 gene, all three restriction endonuclease sites being unique in this vector.

There are several ways to fuse genes to this vector. In addition to the obvious fusion of NarI cohesive ends to NarI, etc., with attention being given to reading frame considerations, it is possible to construct gene fusions in any of the three reading frames using blunt end ligations at the appropriate site. In order to obtain a fusion at the first nucleotide of a reading frame, the vector would be digested with NarI, made blunt ended by a fill-in reaction, then ligated with the blunt ended foreign gene. Similarly, fusions with the second and third nucleotides of a reading frame may be obtained following removal of the 3' overhang resulting from digestion with KpnI or filling in the 5' overhang resulting from Asp718 digestion, respectively. From 4 to 7 amino acids derived from the N-terminus of gG-1 and synthetic oligomer sequences would be fused to the target gene using this vector. The fused gene is then removed from the vector by digestion at the flanking EcoRI and HindIII sites and inserted into the baculovirus gene transfer vector at the desired site, using blunt ends if necessary.

pAcDSM. pAcDSM was designed to allow the insertion of foreign genes into baculoviruses in a form which precisely mimics the batulovirus polyhedrin transcriptional and translational control environment. The construction of pAcDSM has been described in detail above. The vector was modified from pAc373, by replacing the region from nucleotide -9 of the 5' nontranslated leader sequence of the polyhedrin gene to nucleotide +635, (a unique KpnI site) in the polyhedrin coding region with a synthetic oligomer (V78, (SEQ ID NO:3) FIG. 1A) whicn utilizes the existing C from position -9 to complete a PstI site, followed by SacI, SmaI, BamHI, and XbaI sites, and the nucleotides necessary for regeneration of the KpnI site. All of these restriction endonuclease recognition sites are unique in the vector.

Figure 1B:
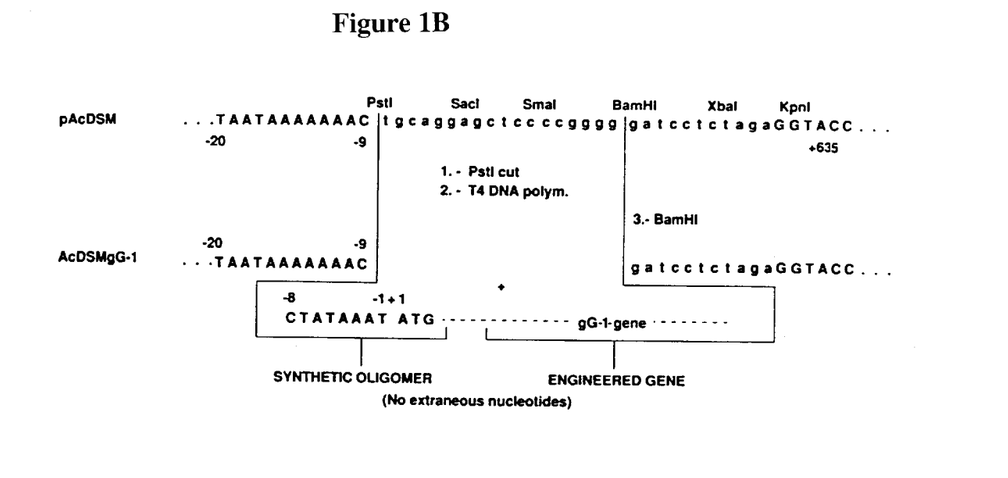

In order to use pAcDSM, it is digested with PstI, treated with T4 DNA polymerase to trim the 3' overhanging nucleotides to a blunt ended C at position -9 of the polyhedrin 5' nontranslated leader sequence, then digested at another restriction site in the polylinker using an enzyme which generates a cohesive terminus, allowing for efficient directional insertion of a foreign gene (FIG. 1B) (SEQ ID NO:6). The foreign gene is modified for compatibility with the vector by assembling a segment of DNA containing, from 5' to 3', the nucleotides -8 to -1 of the 5' nontranslated leader sequence of the polyhedrin gene, the translation initiation codon (SEQ ID NO:7), the coding region of the foreign gene, the downstream region through the polyadenylation signal, and a unique restriction site compatible with one in the transfer vector's polylinker (FIG. 1B). Segments of DNA containing these features can be constructed by using standard cloning techniques and synthetic oligonucleotides as was done here, or by total synthesis using long synthetic oligonucleotides, or by using the polymerase chain reaction with appropriately tailed primers. The insertion of gG-1 and gG-2 into this vector has been described above. When the modified segment of DNA is inserted into pAcDSM prepared as described above, the C in position -9 of the polyhedrin 5' nontranslated leader sequence is linked to the first nucleotide of the modified gene (C in position -8), regenerating the 5' leader sequence of the polyhedrin gene.

Figure 1C:
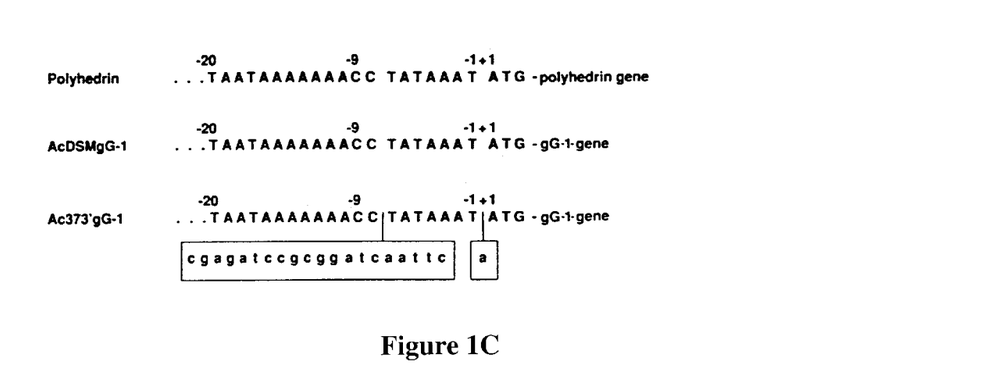

Construction of recombinant baculoviruses expressing gG-1 and gG-2. In order to compare the performance of the vectors described above, two recombinant baculoviruses expressing gG-1 were created, Ac373'gG-1 using pPP-2 in conjunction with pAc373, and AcDSMgG-1 using pAcDSM. Both recombinant baculoviruses differ from wild type AcNPV in the substitution of the gG-1 coding and 3' flanking regions for a portion of the polyhedrin coding region. In addition to these differences. Ac373'gG-1 differs from wild type virus in the 5' nontranslated sequence of the polyhedrin qene by the presence of 21 extraneous nucleotides (SEQ ID NO:9), whereas in AcDSMgG-1 the nucleotide sequence 5' to the translation initiation codon is identical to that of wild type AcNPV (SEQ ID NO:8) (FIG. 1C).

A recombinant baculovirus expressing gG-2, AcDSMgG-2, was created using the transfer vector pAcDSM. As with AcDSMgG-1, AcDSMgG-2 differs from wild-type baculovirus only in the replacement of a portion of the polyhedrin coding sequence with that of the gG-2 coding region, and in the 3' flanking region.

Southern blot analysis. To determine whether the recombinant viruses contained the expected insertions, DNA extracted from recombinant virus infected cells was compared with DNA of transfer vector plasmids and wild type AcNPV. DNAs were digested to completion with SalI, resolved by electrophoresis in agarose and blotted onto nitrocellulose. Replica blots were hybridized with pAc373 and with a probe specific for either the gG-1 or gG-2 genes.

Figure 2A:
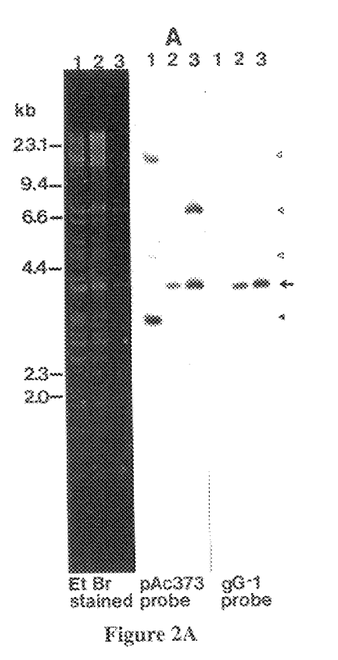
Figure 2B:
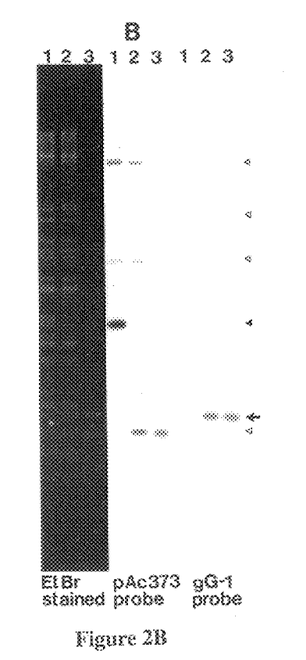

In the transfer vector pAc373'gG-1 and in the recombinant baculovirus Ac373'gG-1, the SaiII fragment containing the gG-1 gene is approximately 3.8 kbp in length, (arrow, FIG. 2A, lanes 2 and 3), and 1.8 kbp in pAcDSMgG-1 as well as in AcDSMgG-1 (arrow, FIG. 2B, lanes 2 and 3). Other bands seen in the hybridization with pAc373 correspond to flanking regions contained in the transfer vector (empty triangles, FIGS. 2A and 2B) as well as the fragment containing the polyhedrin gene in AcNPV (full triangle, FIGS. 2A and 2B). In AcDSMgG-1 an additional 1.6 kbp fragment is seen, in the hybridization with pAc373, which corresponds to the flanking region immediately downstream from gG-1 gene, due to an additional SalI site (FIG. 2B, lanes 2 and 3).

Figure 2C:
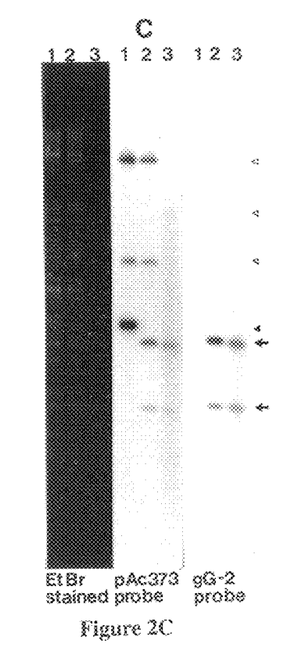

In the recombinant baculovirus and transfer vector carrying the gG-2 gene, bands containing the gG-2 gene appear at approximately 2.8 and 1.9 kbp (arrows in FIG. 2C; a 135 bp fragment is not visible here). The flanking region and polyhedrin gene bands are as described above for Ac373'gG-1.

For all three recombinants the observed hybridization patterns correspond to the ones expected for the intended insertions onto the AcNPV polyhedrin gene.

Figure 3A:
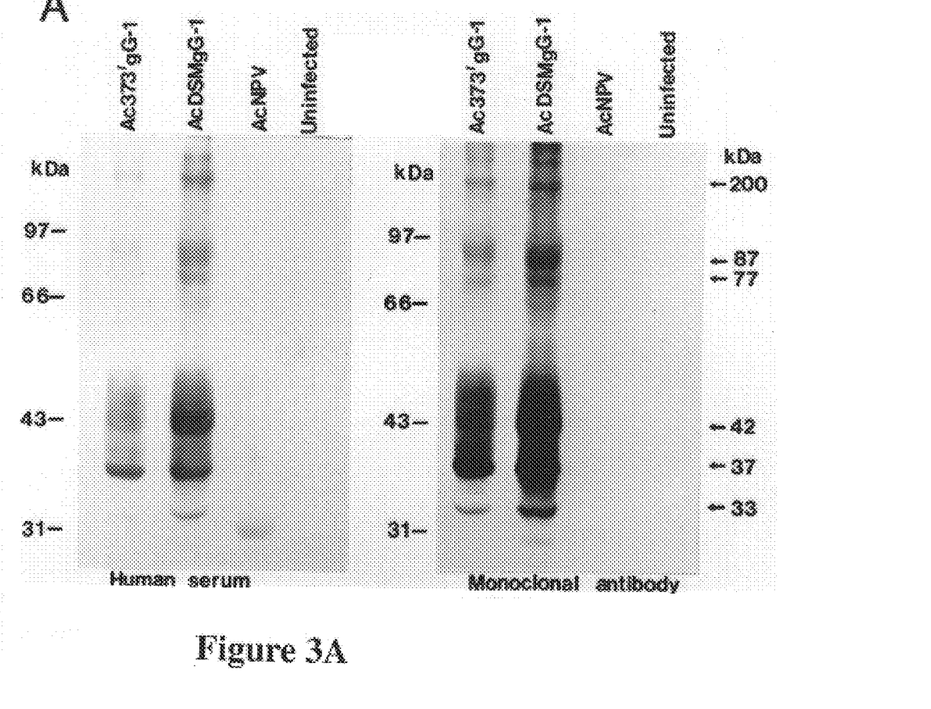

Synthesis and processing of baculovirus expressed qG-1. A 25 cm² flask of confluent Sf9 cells was divided into two flasks, grown overnight, and infected with 10 PFU/cell of either Ac373'gG-1 or AcDSMgG-1. Proteins extracted from numbers of recombinant infected cells harvested at 100 hours post infection (h p.i.), were separated by SDS-PAGE, in parallel with proteins also extracted at 100 h p.i. from AcNPV-infected and uninfected cells. After electrophoretic transfer of the separated proteins onto nitrocellulose membranes, they were reacted with either a human serum specimen which had been identified as HSV-1 positive and HSV-2 negative using an HSV-type specific IHA test (Bernstein and Stewart, Appl. Microbiol. 21:680–684, 1971), or a monoclonal antibody specific for gG-1 (H1379) (FIG. 3A). None of the antibodies reacted with proteins in the lanes containing proteins from AcNPV-infected or uninfected cells, except for a weak reaction between some human serum specimens and polyhedrin in AcNPV-infected cells. The pattern of reactivity with both antibodies was identical in the lanes containing the gG-1-recombinant-infected-cell extracts (lanes Ac373'gG-1 and AcDSMgG-1). The major reacting bands appeared at 37 and 42 kDa apparent molecular mass (37K and 42K) within a region of diffuse reactivity between 36 and 48 kDa apparent molecular mass; weaker bands appeared at 33, 77, 87 and near 200 kDa apparent molecular mass (33K, 77K, 87K, and 200K).

The expression of the recombinant gG-1s differed in two respects: (i) In extracts of Sf9 cells infected with AcDSMgG-1, 42K reacted more than did 37K. In extracts of Sf9 cells infected with Ac373'gG-1 the opposite was true, with 42K being very faint (FIG. 3A). (ii) The intensity of the reaction with both antibodies was higher in extracts of cells infected with AcDSMgG-1 than with Ac373'gG-1 (FIG. 3A).

Figure 3B:
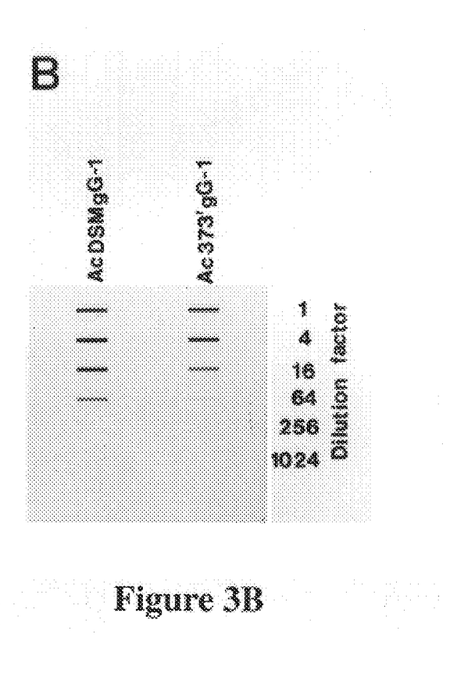

For quantitative comparison of the relative level of expression between the recombinants expressing gG-1, 4-fold-serial dilutions were made of equal portions of identically prepared extracts of Sf9 cells infected at 10 PFU/cell with either Ac373'gG-1 or AcDSMgG-1 and harvested at 100 h.p.i. Extracted proteins bound to a nitrocellulose membrane using a slot-blot apparatus were reacted with gG-1-specific-monoclonal antibody (H1379) and the intensity of their reactions compared. This eliminated difficulties inherent in quantifying multiple diffuse bands in electropherograms. The intensity of the reaction was about 4-fold greater in extracts from cells infected with AcDSMgG-1 than with Ac373'gG-1 (FIG. 3B). A similar result was obtained in a separate experiment using extracts of cells harvested at 72 h p.i. (data not shown). Thus more gG-1 was expressed from the construct which mimicked the AcNPV polyhedrin 5' nontranslated leader sequence (AcDSMgG-1) than from the construct which contained 21 extraneous nucleotides in this region (Ac373'gG-1).

Figure 3C:
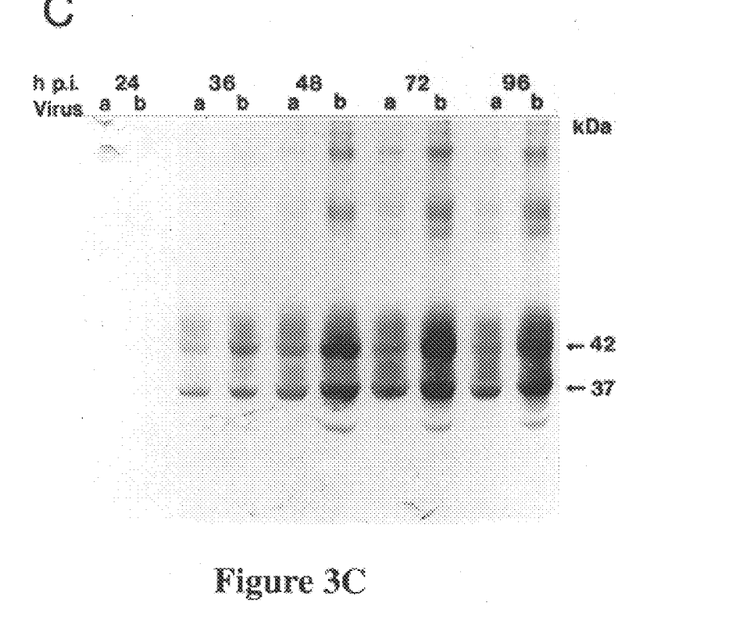

To determine whether the different levels of gG-1 production and the different ratios of intensity between the two major gG-1-bands seen in comparisons of the two recombinants varied with time after infection, equal numbers of Sf9 cells infected in parallel with 10 PFU/cell of either Ac373'gG-1 or AcDSMgG-1 were harvested at 24, 36, 48, 72 and 96 h p.i. After separation of the proteins by SDS-PAGE and transferring them to nitrocellulose, gG-1 was visualized using a HSV-1-positive-human serum specimen (FIG. 3C). The major gG-1 bands (37K and 42K) were first detected at 36 h p.i. At all time points more gG-1 was detected in the lanes containing extracts from cells infected with AcDSMgG-1 (FIG. 3C, lanes b). The maximum expression with both recombinants occurred at about 72 h p.i. As was previously seen at 100 h p.i., at all time points 42K was more abundant than 37K in cDSMgG-1-infected cells (lanes b), while in Ac373'gG-1-infected cells (lanes a), 37K was more abundant than 42K. This indicates that the differences in processing of gG-1 may be due to differences between the transfer vectors.

Figure 3D:
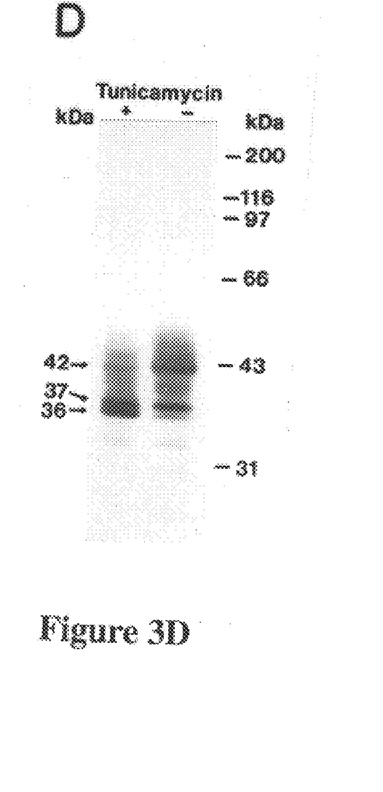

Treatment of AcDSMgG-1 infected Sf9 cells with tunicamycin, an inhibitor of a precursor necessary for N-linked glycosylation (Hemming, Bios. Rep. 2:203–221, 1982), resulted in a great reduction in the intensity of all the bands over 37 kDa apparent molecular mass, most prominently 42K, and an increase in the intensity of an otherwise very faint species of 36 kDA apparent molecular mass. The abundant 37K is of similar intensity in infected cells cultured either in the presence or absence of tunicamycine (FIG. 3D).

Without being bound to any specific theory, the biosynthesis of gG-1 in baculovirus-infected Sf9 cells which accounts for these results, may be explained as follows. 37K is insensitive to tunicamycin and is likely to be the primary nonglycosylated translation product with its signal peptide uncleaved indicating that it was not translocated to the lumen of the rough endoplasmic reticulum. 36K is most abundant during growth in the presence of tunicamycin and would be the nonglycosylated translation product without its signal peptide. The broad band produced by 42K which is sensitive to tunicamycin would be the translation product after having its signal peptide removed and being N-linked glycosylated. 77K, 87K, and 200K are likely to be products of further processing. In heavily loaded gels 77K and 87K were replaced by species of 74kDa and 83kDa apparent molecular mass (data not shown), indicating that the generation of the very high molecular weight gG-1 containing molecules is not dependent on N-linked glycosylation (data not shown). The low abundance 33K species is likely to be the result of proteolytic degradation.

Figure 3E:
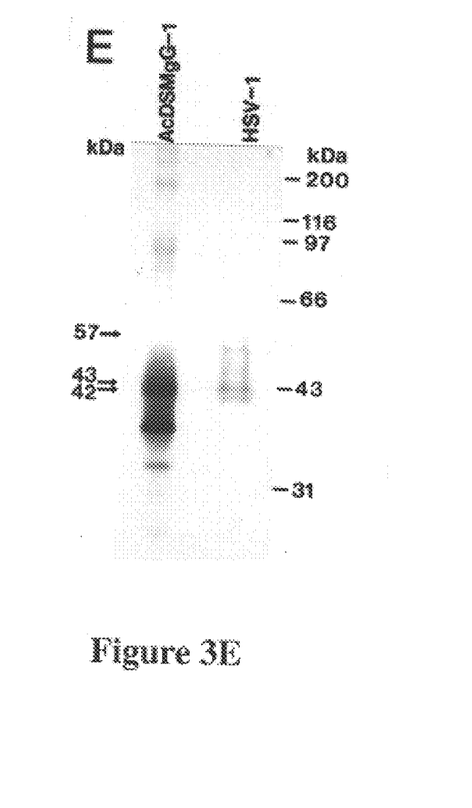

To compare baculovirus and HSV-1 expressed gG-1, extracts from HSV-1(F)-infected-HEp-2 cells and AcDSMgG-1-infected-Sf9 cells were separated by SDS-PAGE, transferred onto nitrocellulose and reacted with gG-1-specific monoclonal antibody. Major bands with apparent molecular masses of 42 and 43 kDa (42K and 43K) and a smear between 50 and 57 kDa apparent molecular mass were found in extracts of HEp-2 cells infected with HSV-1(F) (FIG. 3E). In heavily loaded gels the smear extended to 66 kDa apparent molecular mass (not shown). As also seen in FIG. 3A, strongly reactive 37K and 42K species within a region of diffuse reactivity between 36 and 48 kDa apparent molecular mass were detected in Sf9 cells infected with AcDSMgG-1; weaker reactions were observed with 33K, 77K, 87K, and 200K.

Figure 4A:
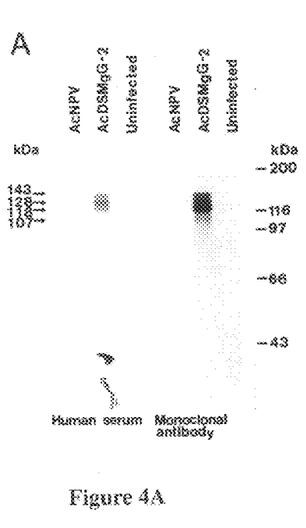

Synthesis and processing of baculovirus expressed gG-2. Extracts of Sf9 cells infected with 10 PFU/cell of AcDSMgG-2 harvested at 100 h p.i. were separated by SDS-PAGE in parallel with extracts of AcNPV-infected and uninfected cells. The separated proteins were transferred onto nitrocellulose membranes. Replicas of this set were reacted with either a HSV-2-positive- and HSV-1-negative-human serum specimen, or with a gG-2-specific monoclonal antibody (H1206) (FIG. 4A). In lanes containing extracts from AcDSMgG-2 infected cells, both antibodies reacted with bands with apparent molecular masses of 107, 118, 128, and 143 kDa (107K, 118K, 128K, and 143K). The human serum specimen reacted most strongly with 128K; and the monoclonal antibody with 118K. This difference in reactivity between the human serum and the monoclonal antibody is not a general phenomenon, inasmuch as other human serum specimens reacted most strongly with 118K (data not shown).

Figure 4B:
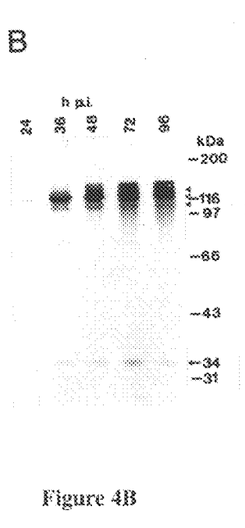
Figure 4C:
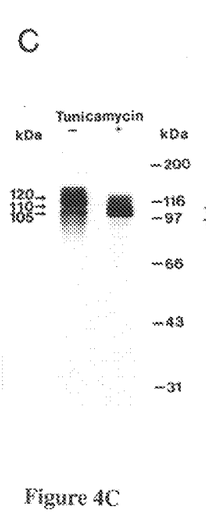

To monitor expression of gG-2 in recombinant baculovirus infected cells, Sf9 cells infected with AcDSMgG-2 at 10 PFU/cell were harvested at 24, 36, 48, 72 and 96 h p.i. Infected cell proteins were separated by PAGE, transferred onto nitrocellulose membranes, and reacted with a gG-2-specific monoclonal antibody (FIG. 4B). Only one band (118K, empty triangle) was detected at the earliest time point examined (24 h.p.i.). By 36 h p.i. it had increased in intensity and two faint bands appeared (107K and 128K, full triangles). From 48 h p.i. onward the four bands (107K, 118K, 128K, and 143K) previously seen at 100 h p.i. (FIG. 4A) were visible, with the maximum accumulation of protein occurring at 72 h p.i. A weakly reactive protein with an apparent molecular mass of 34 kDa (34K, arrow) whose relative abundance varies from preparation to preparation was first detected at 36 h p.i.

Figure 5:
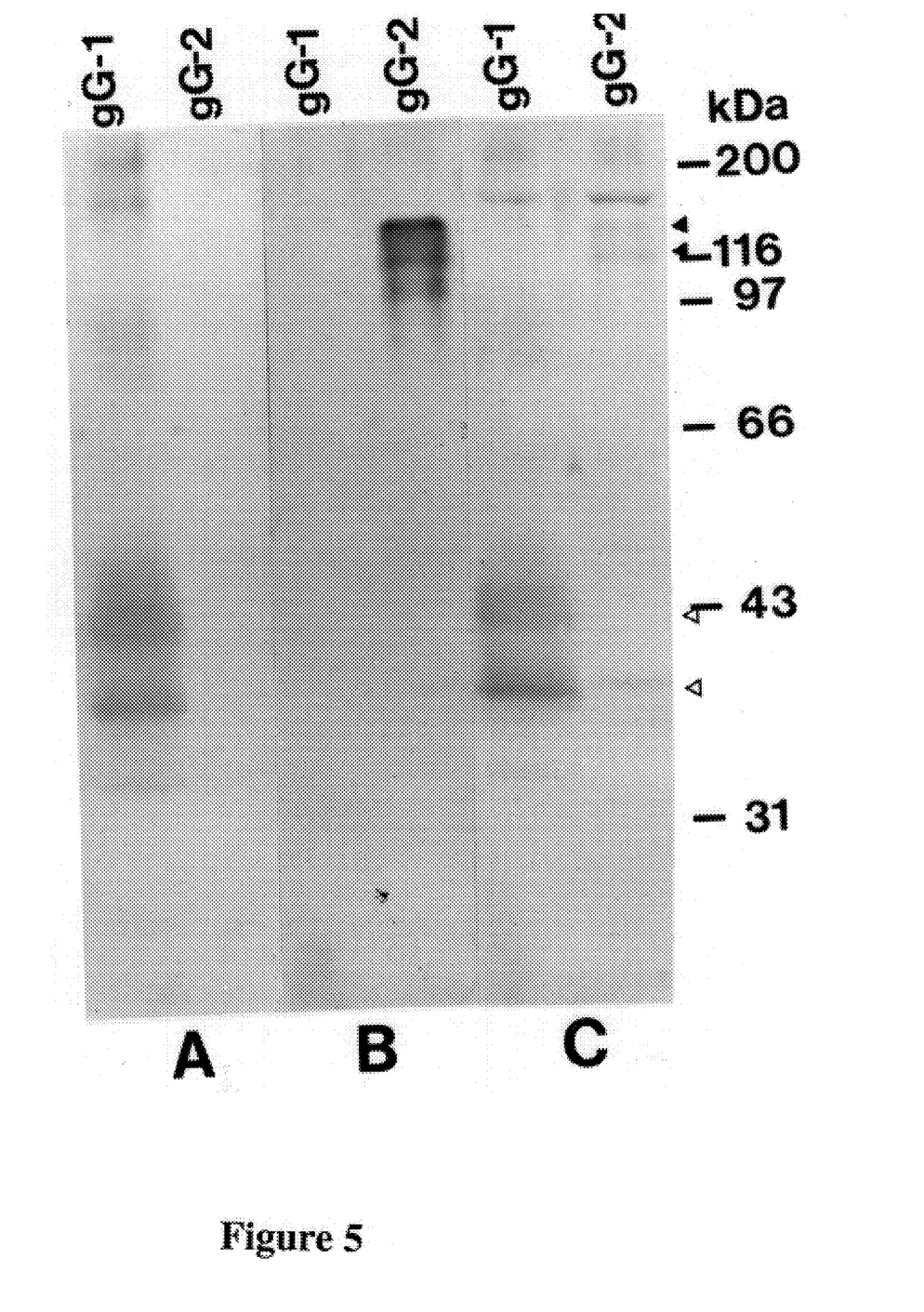
FIG. 5 shows the immunoblot analysis of the HSV type-specificity of the reaction of human serum specimens with AcDSMgG-1- and AcDSMgG-2-infected-Sf9-cell extracts. Proteins were separated by SDS-PAGE in a 11% gel, transferred to nitrocellulose, then reacted with serum specimens known to be HSV-1 positive and HSV-2 negative (A), HSV-1 negative and HSV-2 positive (B) and low positive titer to both HSV-1 and HSV-2. Bands considered to be diagnostic for HSV-1 specific reactivity are indicated with empty triangles, and those for HSV-2 with full triangles. Electrophoretic conditions and molecular mass standards were as for FIG. 3.

In the electrophoretic pattern of extracts of Sf9 cells infected with AcDSMgG-2 treated with tunicamycin, bands migrating with apparent molecular masses of 105, 110 and 120 kDa (105K, 110K, and 120K) were present compared with the untreated cell species 107K, 118K, 128K and 143K (FIG. 5C). In overloaded SDS-PAGE gels, a band migrating with an apparent molecular mass of 30 kDa was present in contrast with the 34K species seen in untreated cells (data not shown).

Without being bound to any specific theory, the biosynthesis of gG-2 in baculovirus-infected Sf9 cells, which accounts for these results, may be explained as follows. 107K is the primary translation product including the signal peptide. This is based on two observations. (i) It is synthesized in the absence of tunicamycin. (ii) Since no species migrating faster than 105K were detected in cells infected in the presence of tunicamycin, 107K is inferred not to be N-linked glycosylated, therefore likely to be unaffected by tunicamycin treatment, and is probably obscured by the other species in the gel. 105K is the primary translation product after cleavage of its signal peptide based on its increase in abundance in the presence of tunicamycin. The tunicamycin-sensitive 118K is the cleaved primary translation product after N-linked glycosylation. 128K and 143K, and 110K and 120K, synthesized in the absence or presence, respectively, of tunicamycin are possibly the products of 0-linked glycosylation. The tunicamycin sensitive 34K which was found in some preparations is likely to be the result of a specific cleavage or proteolytic degradation.

Figure 4D:
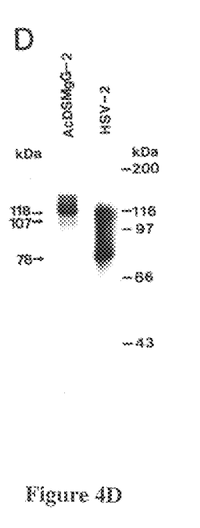

To compare baculovirus and HSV-2 expressed gG-2, extracts from HSV-2(G)-infected-HEp-2 cells and AcDSMgG-2-infected-Sf9 cells were reacted with a gG-2-specific monoclonal antibody after separation by SDS-PAGE and transfer to nitrocellulose (FIG. 4D). In the lane containing extracts from HEp-2 cells infected with HSV-2 (G), a smear of reactivity was seen ranging from an apparent molecular mass of 78 through 118 kDa with distinctive species at 78, 107 and 118 kDa apparent molecular mass. In the electrophoretic pattern of proteins extracted from Sf9 cells infected with AcDSMgG-2, the 107K, 118K, 128K and 143K species were detected.

HSV-type specificity of the reaction of human serum specimens with the baculovirus expressed proteins. Proteins in extracts of Sf9 cells expressing the recombinant gG-1 or gG-2 were separated by SDS-polyacrylamide gel electrophoresis, transferred onto nitrocellulose, and reacted with ten different human serum specimens previously characterized by using HSV-type specific indirect hemagglutination assays (IHA) (Bernstein and Stewart, supra). The patterns obtained with three of these ten specimens are shown in FIG. 5. Using the gG-1 37K and 42K species, and the gG-2 118K species, plus either or both of the 128K and 143K species, as markers of HSV-1 and HSV-2 type specific reaction, respectively, a serum specimen positive for HSV-1 and negative for HSV-2 by IHA, and a serum specimen positive for HSV-2 and negative for HSV-1 by IHA, each reacted in a type-specific manner in the immunoblot assay (FIGS. 5A and B, respectively). A serum specimen weakly positive for both types of antibodies by IHA reacted with the gG-1 specific 37K and 42K species (empty triangles) in the lane of the recombinant gG-1, and reacted weakly but clearly with the gG-2 118K and 128K species (full triangles) in the lane containing recombinant gG-2 (FIG. 5C). The other serum specimens tested also reacted in a type-specific manner with the recombinant gG-1 and gG-2 in agreement with the IHA results (data not shown).

Various patterns of weak reactivity were seen between human serum specimens and extracts of wild type baculovirus infected Sf9 cells as well as uninfected cells. The faint bands seen at 36 kDa apparent molecular mass in the gG-2 lanes of FIG. 5, as well as the bands seen at 170 kDa apparent molecular mass in FIG. 5C, are examples of these reactions. However, in no case was the reactivity of such an extent or nature so as to lead to ambiguity in interpretation.

Advantages of the baCulovirus gene expression system. To determine whether higher levels of gene expression in the baculovirus system would be obtained from constructs which mimic the control sequences of the highly expressed polyhedrin gene, as noted above two gene transfer vector systems were used to express gG-1: one which precisely mimics the wild type baculovirus transcriptional and translational control environment, and one which contains 21 extraneous nucleotides in the 5' nontranslated leader sequence (FIG. 1C). Four-fold greater expression was observed from the construct which perfectly mimics the wild type virus control regions. The availability of the pAcDSM transfer vector will allow careful dissection of the environment in the vicinity of the translation initiation codon through the construction of viruses with precise sequence modifications in this region.

Unexpectedly, in addition to the difference in the level of expression between the two gG-1 expressing recombinants, a significant difference was observed in the ratio of nonglycosylated precursor (37K, vide infra) to glycosylated product (42K), with gG-1 expressed from AcDSMgG-1 being the most efficiently processed. Inasmuch as the gG-1 coding sequence was not altered during the construction of the recombinants, these results indicate a noticeable effect on gG-1 processing by the structure of its mRNA. Without being bound to any particular hypothesis, it is postulated that the 21 extraneous nucleotides in the 5' nontranslated leader sequence of the MRNA of the less efficiently processed protein interfere with the interaction of signal recognition particle with the nascent polypeptide chain, ultimately resulting not in the translational complex being translocated to the endoplasmic reticulum for membrane insertion and glycosylation, but in nonmembrane associated translation resulting in cytoplasmic accumulation of unprocessed cytoplasmic full length precursor gG-1.

It is further found that the biosynthesis of gG-1 in baculovirus infected insect cells differs in several respects from its synthesis in mammalian cells infected with HSV-1 or gG-1-expressing vaccinia virus recombinants. In infections with HSV-1, tunicamycin-insensitive products of 39 and 44 to 48 kDa (Ackermann et al, Virology 150:207–220, 1986; Frame et al, J. Gen. Virol. 67:745–751, 1986; Richman, J. Virology 57: 647–655, 1986) apparent molecular mass have been observed. The 44 to 48 kDa species undergoes processing to a highly glycosylated tunicamycin-sensitive product which migrates as a diffuse band with an apparent molecular mass of 59 to 68 kDa (Ackermann et al, Virology 150:207–220, 1986; Frame et al, J. Gen. Virol. 67:745–751, 1986; Richman et al, J. Virology 57:647–655, 1986). In a direct comparison of baculovirus and HSV-1 expressed gG-1 (FIG. 3E), products were observed with apparent molecular masses of 42 and 43 kDa in HSV-1 infected cells which comigrated with 42K. It is possible that the 42 and 43 kDa species found in HSV-1 infected cells correspond to the 44 to 48 kDa species reported by others using the same strain of virus (strain F) and the same monoclonal antibody (H1379). The relationship between these products and the closely migrating products found in the baculovirus infected cells is not clear, however, inasmuch as the baculovirus protein is tunicamycin sensitive and thus glycosylated, as is a product of similar size found in cells infected with a vaccinia virus/gG-1 recombinant, while the HSV-1 product is poorly labeled with glucosamine. In addition, a similarly sized product is synthesized in the presence of tunicamycin in HSV-1 strain HFEM-infected cells. No high molecular mass products similar to 77K, 87K, 200K have been found in HSV-infected cells.

Biosynthesis of gG-2. As with gG-1, there were significant differences between the biosynthesis of gG-2 in baculovirus infected insect cells and in HSV-1 infected mammalian cells. In both baculovirus and HSV-2 infected cells, a tunicamycin-sensitive product of 118 kDa apparent molecular mass is synthesized. In baculovirus infected cells it appears that this product is processed further into higher molecular mass forms, but in HSV-2 infected cells this product is cleaved to generate 31K (Su et al, J. Virol. 61:1735–1737, 1987) and 74K (Balchandran and Hutt-Fletcher, J. Virol. 54:825–832, 1985) fragments. 74K is subsequently 0-linked glycosylated yielding 105K (Balachandran and Hutt-Fletcher, 1985). 31K is further glycosylated to 34K, which is efficiently secreted from infected cells (Su et al, 1987). The 34K species in baculovirus-infected cells differs from the similarly sized product in HSV-2 infected cells in that the baculovirus product is found intracellularly and the HSV-2 product is found extracellularly.

Several differences in the synthesis and processing of gG-1 and gG-2 relative to that observed here and by others during infections with HSV reflect differences in rotein processing mechanisms between insect and mammalian cells. In spite of these differences, the recombinant proteins are efficiently recognized in a HSV type specific manner by human serum specimens. The retention of the type specificity of their natural counterparts, the reduced biohazard during large-scale production, and the ability to produce large amounts of antigen efficiently now make accurate, simple and reliable HSV-type specific serologic tests widely available.

Substantially pure, type-specific antigens (gG-1 and gG-2) of the present invention are obtained by isolating and purifying these antigens from other cellular products or components by conventional isolation and purification techniques well known to one of ordinary skill in the art.

Type-specific serologic tests are performed by reacting a sample of the biological fluid (such as blood, serum, plasma, etc.) obtained from a person suspected of HSV infection, with gG-1 and gG-2 antigens of the present invention and determining the resultant formation of immunocomplex, the formation of immunocomplex with gG-1 being indicative of HSV-type 1 infection and the formation of immunocomplex with gG-2 being indicative of HSV-type 2 infection. Cross-reactivity between gG-1 and gG-2 has not been detected in human serum specimens.

A diagnostic kit for the detection of type-specific HSV infection, comprises at least separate non-cellular (artificial) containers separately containing the gG-1 and gG-2 antigens of the present invention in substantially pure form and instructional material to perform the diagnostic test. The kit may also include other conventional items such as microtiter plates, micropipettes and the like which are commonly found in such kits.

The type-specific antigens of the present invention are also useful in a composition which comprises an immunoreactive amount of the gG-1 and gG-2 antigens of the present invention in a pharmaceutically acceptable carrier.

Given the substantially pure antigens gG-1 and gG-2 of the present invention, monoclonal antibodies (MAbs) of particular specificity are made by standard techniques well known to one of ordinary skill in the art (Yelton & Scharff, Ann. Rev. Biochem. 50:657–680, 1981). Such monoclonal antibodies are useful in identifying the presence of HSV or HSV-antigens of particular types. A kit comprising separate containers containing the type-specific MAbs are useful in detecting the presence of HSV or HSV antigens in a biological sample.

Of course, having illustrated the efficient, high level expression of two heterologous proteins (gG-1 and gG-2) by the recombinant baculoviruses of the present invention, expression of other foreign proteins is similarly achieved by the methodologies described herein as will be suggested to one of ordinary skill in the art.

It is understood that the examples and embodiments described herein are for illustrative purposes only and that various modifications or changes in light thereof will be suggested to persons skilled in the art and are to be included within the spirit and purview of this application and scope of the appended claims.

We claim:

1. A diagnostic kit comprising containers separately containing recombinant baculovirus expressed herpes simplex virus gG-1 and herpes simplex virus gG-2 antigens in substantially pure form, wherein the herpes simplex virus gG-1 and herpes simplex virus gG-2 antigens are produced by employing a recombinant baculovirus having the 5' nontranslated leader sequence of the polyhedrin gene joined to the coding region of a foreign gene precisely at the translation initiation codon of the polyhedrin gene, without either missing any nucleotide present in said initiation codon or introducing any extraneous nucleotide at the initiation codon site.

2. A diagnostic assay for detecting type-specific herpes simplex virus infection comprising contacting a biological sample obtained from a person suspected of herpes simplex virus infection with substantially pure recombinant baculovirus expressed herpes simplex virus gG-1 and herpes simplex virus gG-2 antigens, wherein the herpes simplex virus gG-1 and herpes simplex virus gG-2 antigens are produced by employing a recombinant baculovirus having the 5' nontranslated leader sequence of the polyhedrin gene joined to the coding region of a foreign gene precisely at the translation initiation codon of the polyhedrin gene, without either missing any nucleotide present in said initiation codon or introducing any extraneous nucleotide at the initiation codon site, and detecting any immunocomplex formed, the formation of an immunocomplex with said herpes simplex virus gG-1 antigen being indicative of herpes simplex virus type 1 infection and the formation of an immunocomplex with said herpes simplex virus gG-2 antigen being indicative of herpes simplex virus type 2 infection.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:

(A) LENGTH: 36 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:1:

AATTCTATAA ATAATGTCGC AGGGCGCCCG GTACCA                      36

(2) INFORMATION FOR SEQ ID NO:2:

(i) SEQUENCE CHARACTERISTICS:
            (A) LENGTH: 36 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:2:

AGCTTGGTAC CGGGCGCCCT GCGACATTAT TTATAG                      36

(2) INFORMATION FOR SEQ ID NO:3:

(i) SEQUENCE CHARACTERISTICS:
            (A) LENGTH: 34 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:3:

TGCAGGAGCT CCCCGGGGGA TCCTCTAGAG GTAC                        34

(2) INFORMATION FOR SEQ ID NO:4:

(i) SEQUENCE CHARACTERISTICS:
            (A) LENGTH: 29 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:4:

CGCCCTGCGA CATATTTATA GGTACCAAT                              29

(2) INFORMATION FOR SEQ ID NO:5:

(i) SEQUENCE CHARACTERISTICS:
            (A) LENGTH: 40 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:5:

AGCTTGGTAC CTATAAATAT GCACGCCATC GCTCCCTGCA                  40

(2) INFORMATION FOR SEQ ID NO:6:

(i) SEQUENCE CHARACTERISTICS:
            (A) LENGTH: 47 base pairs
            (B) TYPE: nucleic acid
            (C) STRANDEDNESS: single
            (D) TOPOLOGY: linear -continued (ii) MOLECULE TYPE: DNA (genomic)

(xi) SEQUENCE DESCRIPTION: SEQ ID NO:6:

TAATAAAAAA ACTGCAGGAG CTCCCCGGGG GATCCTCTAG AGGTACC                47

(2) INFORMATION FOR SEQ ID NO:7:

(i) SEQUENCE CHARACTERISTICS:
        (A) LENGTH: 11 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:7:

CTATAAATAT G                                                      11

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:8:

TAATAAAAAA ACCTATAAAT ATG                                         23

(2) INFORMATION FOR SEQ ID NO:9:

(i) SEQUENCE CHARACTERISTICS:
        (A) LENGTH: 44 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:9:

TAATAAAAAA ACCCGAGATC CGCGGATCAA TTCTATAAAT AATG                  44